United States Patent [19]

Kovacs, Jr. et al.

[11] Patent Number: 4,503,331
[45] Date of Patent: Mar. 5, 1985

[54] NON-CIRCULAR EMISSION COMPUTED TOMOGRAPHY

[75] Inventors: Richard M. Kovacs, Jr., Monroe, Conn.; Eugene J. Senger, Chagrin Falls; Robert H. Wake, Solon, both of Ohio

[73] Assignee: Technicare Corporation, Solon, Ohio

[21] Appl. No.: 370,425

[22] Filed: Apr. 21, 1982

[51] Int. Cl.³ .............................................. G01T 1/20
[52] U.S. Cl. ............................................... 250/363 S
[58] Field of Search ............. 250/363 S, 360.1, 361 R, 250/491.1; 378/11, 20

[56] References Cited

U.S. PATENT DOCUMENTS

| | | |
|---|---|---|
| 1,599,696 | 9/1926 | Wantz . |
| 2,595,260 | 5/1952 | Hollstein . |
| 3,011,057 | 11/1961 | Anger . |
| 3,281,598 | 10/1966 | Hollstein . |
| 3,617,749 | 11/1971 | Masslot . |
| 3,697,751 | 10/1972 | Tschunt . |
| 3,756,549 | 9/1973 | Lange . |
| 3,845,308 | 10/1974 | Cattrell . |
| 4,064,441 | 12/1977 | Casale . |
| 4,150,297 | 4/1979 | Borggren . |
| 4,216,381 | 8/1980 | Lange . |
| 4,223,222 | 9/1980 | Gray et al. . |
| 4,400,620 | 8/1983 | Blum ............................ 250/363 S |
| 4,401,890 | 8/1983 | Blum ............................ 250/363 S |
| 4,445,035 | 4/1984 | Ueyama ........................ 250/363 S |

FOREIGN PATENT DOCUMENTS 1175032 12/1969 United Kingdom .
1572809 8/1980 United Kingdom .

OTHER PUBLICATIONS

DYMAX LF Gamma Camera, by Elscint, Inc., Hackensack, NJ 07602.
The Flexible Concept in Gamma Cameras, The XL-91 Detector, Raytheon Medical Electronics, 70 Ryan St., Stamford, CT 06907.
Pho/gamma LFOV Large Field of View Scintillation Camera, Searle Radiographics, Inc.
DYNACamera 4, Picker Corporation, 595 Miner Road, Cleveland, OH 44143.
MaxiCamera 400 T, General Electric.
Sigma 400 sigma 410S and sigma 438, Technicare Corporation, 29100 Aurora Road, Solon, OH 44139.

Primary Examiner—Janice A. Howell
Attorney, Agent, or Firm—M. A. Kaufman

[57] ABSTRACT

A radiation imaging system including a rotatable scintillation detector for non-circular emission computed tomography. The radiation imaging system includes a rotatable scintillation detector and a linearly movable detector stand. With the stand stationary, the scintillation detector is capable of circularly orbiting about the longitudinal axis of the patient for emission computed tomography and with the detector stationary the detector stand may be linearly displaced for whole body scanning with the patient aligned parallel to the detector stand path in an orientation orthogonal to the tomographic orientation. The circular rotational motion is combined with the linear translation such that the detector orbits about a section of the patient in a non-circular path. The path assures a minimum distance between the face of the scintillation detector and the boundary of the patient during the entire tomographic orbit to thereby improve resolution of the tomogram.

12 Claims, 5 Drawing Figures

NON-CIRCULAR EMISSION COMPUTED TOMOGRAPHY

TECHNICAL FIELD

This invention relates to radiation imaging devices and in particular to a system for performing emission computed tomography with a scintillation detector rotated in a non-circular orbit about a patient.

BACKGROUND ART

In nuclear medicine, a radionuclide is administered to a patient and a scintillation camera such as the Anger gamma camera, shown in U.S. Pat. No. 3,011,057, is used to produce a visual image of the distribution of the administered radionuclide within the target organ of the patient. Devices used to detect the emitted radiation utilize a collimator to selectively filter the passage of emitted radiation from the patient to a scintillation system which includes a scintillation crystal positioned behind the collimator. The crystal changes radiation to visible light during each scintillation.

The gamma rays that do not pass through the collimator do not contribute to the image. Spatial resolution is approximately proportional to the depth of the object, that is, the distance between the object and the face of the collimator. For planar imaging, this distance is minimized by placing the collimator as close as possible to the portion of the patient being imaged. To perform three dimensional imaging, such as emission computed tomography (ECT), it is necessary to have the detector portion of the radiation imaging device orbit the patient. Scintillation cameras capable of emission computed tomographic studies, such as Technicare's Omega 500, are arranged to have the scintillation detector orbit the patient in a circular path. Since people tend to have an elongated circumference at thorax level, a circular orbit will necessarily result in undesirable separation between the face of the collimator and the patient's chest (anterior position) and patient's back (posterior position). During these portions of the circular orbit, the patient-detector distance will be undesirably excessive. Hence, the resolution of the reconstructed tomographic image will be degraded relative to a tomogram acquired from an orbital path closely tracking the patient's perimeter.

DISCLOSURE OF THE INVENTION

We have invented a system wherein a scintillation detector capable of both rotational tomographic studies and whole body scanning studies is modified such that the detector is rotatable about a circumference of the patient in a highly efficient path closely approximating the boundary of the patient at the desired circumference. The improved path is non-circular, for example, elliptical and is achieved by synchronously combining the rotational and translational capabilities of the detector.

DESCRIPTION

Figure 1:
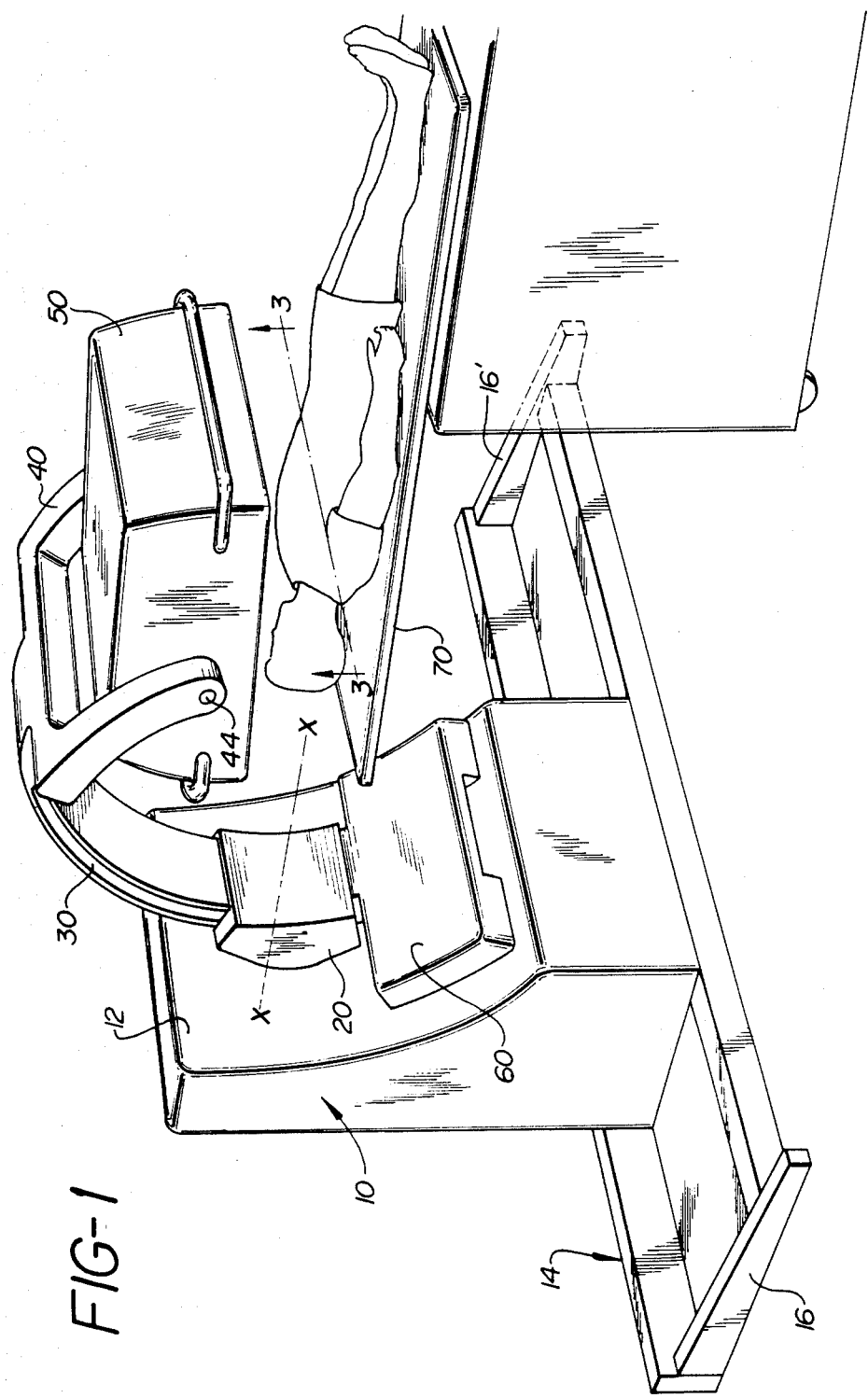
FIG. 1 is a perspective view of a scintillation camera in which the detector is adapted for tomographic studies by circularly orbiting about a patient as well as performing whole body studies by linearly translating the base supporting the scintillation detector.
Figure 2:
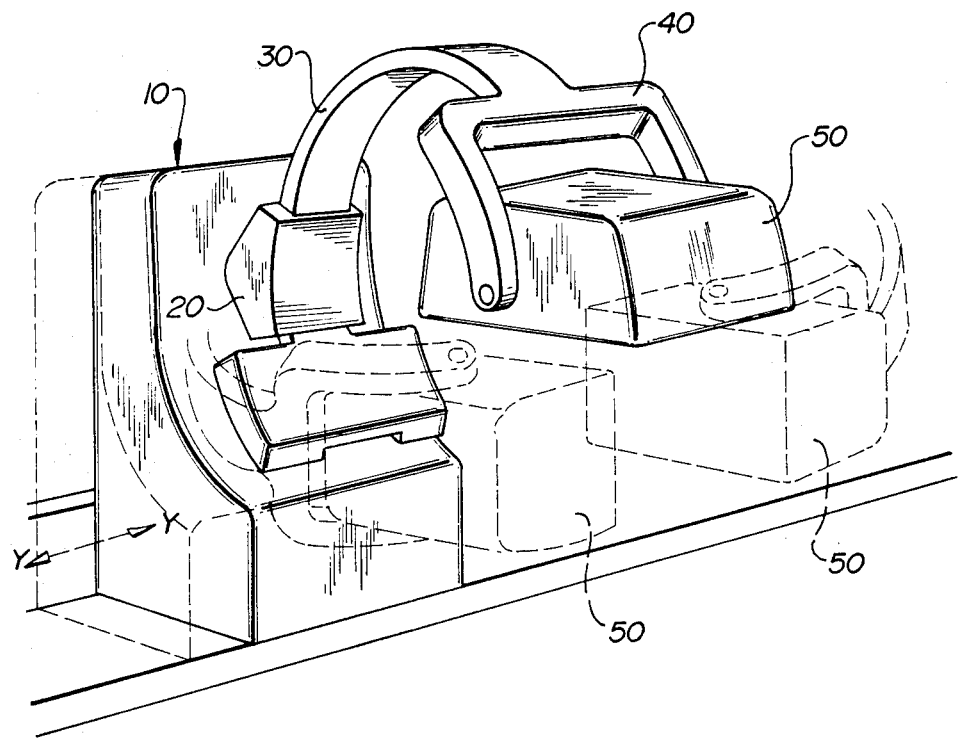
FIG. 2 is also a perspective view of the scintillation camera of FIG. 1 showing the detector rotated in phantom about a representative circular orbit as well as showing the translational capability of the entire structure also in phantom.

Referring first to FIGS. 1 and 2, there is shown a scintillation camera of the type capable of both linear translational motion for use in whole body scanning studies and orbital motion for tomographic studies, the structure for which is described in commonly assigned application Ser. No. 195,269; filed Oct. 8, 1980 now U.S. Pat. No. 4,426,578. Though the invention is described in connection with that structure, in principle, it could be used in concert with virtually any imaging system in which a detector is adapted to circumscribe an object.

Briefly, the camera includes a scintillation detector supported by a C-arm and a detector stand. Specifically, the apparatus comprises a detector stand such as base member 10 which has a generally cubic appearance except for a curved frontal portion 12. In whole body studies, the base member 10 is moved along an area scan platform 14, along axis Y—Y, as shown in phantom in FIG. 2. In static and tomographic studies, such as circular ECT, the base member 10 is stationary.

Attached to the frontal portion 12 of base member 10 is a carrier member 20 which is rotatable about an axis X—X parallel to the longitudinal orientation of a patient support 70 and orthogonal to lateral axis Y—Y. The carrier member is arcuate and has a wide central groove therein for engaging a C-shaped support member or C-arm 30. At one end of C-arm 30 there is provided a yoke 40 to which a scintillation detector 50 is pivotally attached by means of ball bearings 44. The pivotal attachment permits the detector 50 to be positioned in a desired orientation relative to the patient. To vary the distance between the face of the detector 50 and the patient, the C-arm 30 is moved relative to carrier member 20, thus altering the radius with which the detector orbits the patient. Attached to the other end of C-arm 30 is a counterweight 60 which functions to assure that C-arm 30 remains fixed in relation to carrier member 20 at any desired point along the circular segment to which the detector is positioned.

Figure 3:
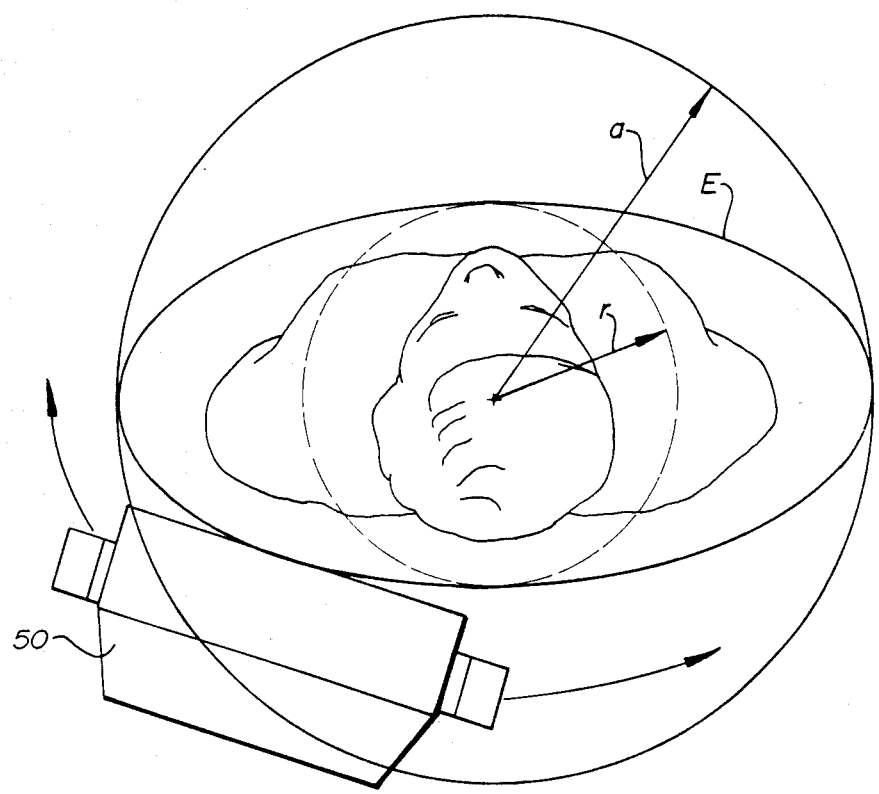
FIG. 3 is a section taken along line 3—3 of FIG. 1 showing the scintillation detector obriting the patient in a non-circular path, i.e., a plane corresponding to a transverse section through the patient.

A path of orbital rotation of the scintillation detector 50 is illustrated in FIG. 2. The orbital radius may be altered by moving C-arm 30 relative to carrier member 20. FIG. 3 shows an orbital circle of radius a circumscribing a patient in the normal supine orientation for examination. If the detector 50 were to follow the circumferential path of circle of radius a, the face of the detector would be relatively close to the patient adjacent to either arm, but the detector would be relatively far from the patient in both the anterior and posterior positions. However, a smaller circle of, for example, radius r, though efficient in the anterior and posterior orientations is unacceptable because it would cut through the patient during the remaining portions of the orbit. The elliptical orbit E shown in FIG. 3 of semi-minor axis r and semi-major axis a defines a preferred path for the scintillation detector's rotation.

Figure 4:
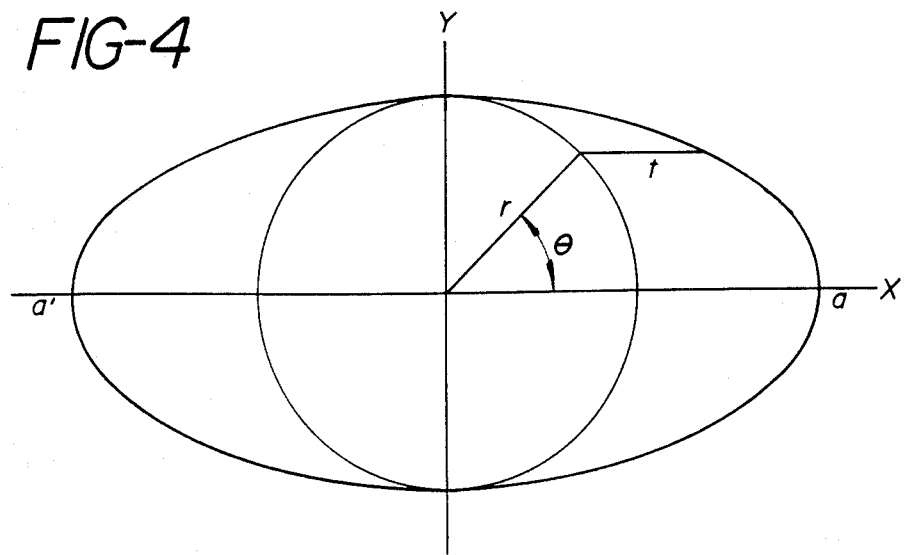
FIG. 4 illustrates geometrically the combined rotational and translational motions that yield the non-circular orbital path of the scintillation detector in FIG. 3.

As shown in the geometric illustration of FIG. 4, the ellipse of FIG. 3 is equivalent to a circle of radius r augmented by some linear segment t parallel to the major axis, where the length of t is a function of angle $\theta$. Specifically, the ellipse of semi-major axis a and semi-minor axis r is related to a circle of radius r by means of the horizontal segment t in accordance with the following relationship:

$$t = (a-r)\cos\theta \qquad (1)$$

To trace the same ellipse in terms of increments $d\theta$ of the angle $\theta$, the following relationship holds:

$$dt = -(a-r)\sin\theta d\theta \qquad (2)$$

Since the scintillation camera is capable of both the circular orbital rotation about axis X—X and linear translational motion along axis Y—Y, and hence, parallel to the semi-major axis of the ellipse, and since the ellipse may be traced in increments of orbital rotation ($d\theta$) and lateral translation (dt), the desired elliptical perimeter may be traced.

In operation, to implement, for example, an elliptical orbit, the translation of the base member 10 is synchronized with the rotation of the carrier member 20 and C-arm 30 such that for every increment of rotation ($d\theta$), the base member is linearly displaced an incremental distance (dt). Preferably, the incremental rotation ($d\theta$) and the incremental translation (dt) are accomplished simultaneously; however, these motions can of course be independent and alternate. In the preferred embodiment, there are intermittent pauses in the orbital path of the detector for data acquisition. If desired, however, the rotation may be continuous. Furthermore, whether the rotation is intermittent or continuous, the rotation and translation may be in unison or alternating.

A variety of techniques of two general categories could be employed to define the specific path that the scintillation detector will follow during its orbit about a patient. One category is to prescribe a specific path before the orbit is initiated and the other category is to use a feedback control system to monitor and adjust the detector's path in mid-course.

One alternative in the first category is to have the operator physically position the scintillation detector to a minimum circular radius that is coincident with the semi-minor axis to establish the value of r and then to physically move the stand linearly along its base and rotate the detector into a position coincident with position a to establish the maximum orbital length, wherein $a = r + t_{max}$. With this information physically obtained, the scintillation camera system can be preprogrammed to trace the desired elliptical path. An alternative technique in the first category is to measure the patient's width and thickness at the location where the tomographic study is to be performed and based on these measurements have the operator select the optimum orbit from an available list of orbits.

Alternatively, the path followed by the orbiting scintillation detector could be established in mid-course. In this category of techniques, the scintillation detector stand is positioned at the point where the study is to be initiated. The detector is equipped with a patient proximity sensor which tracks the outline of the patient and support table 70 and follows a predefined minimum patient-detector distance during the orbit.

Figure 5:
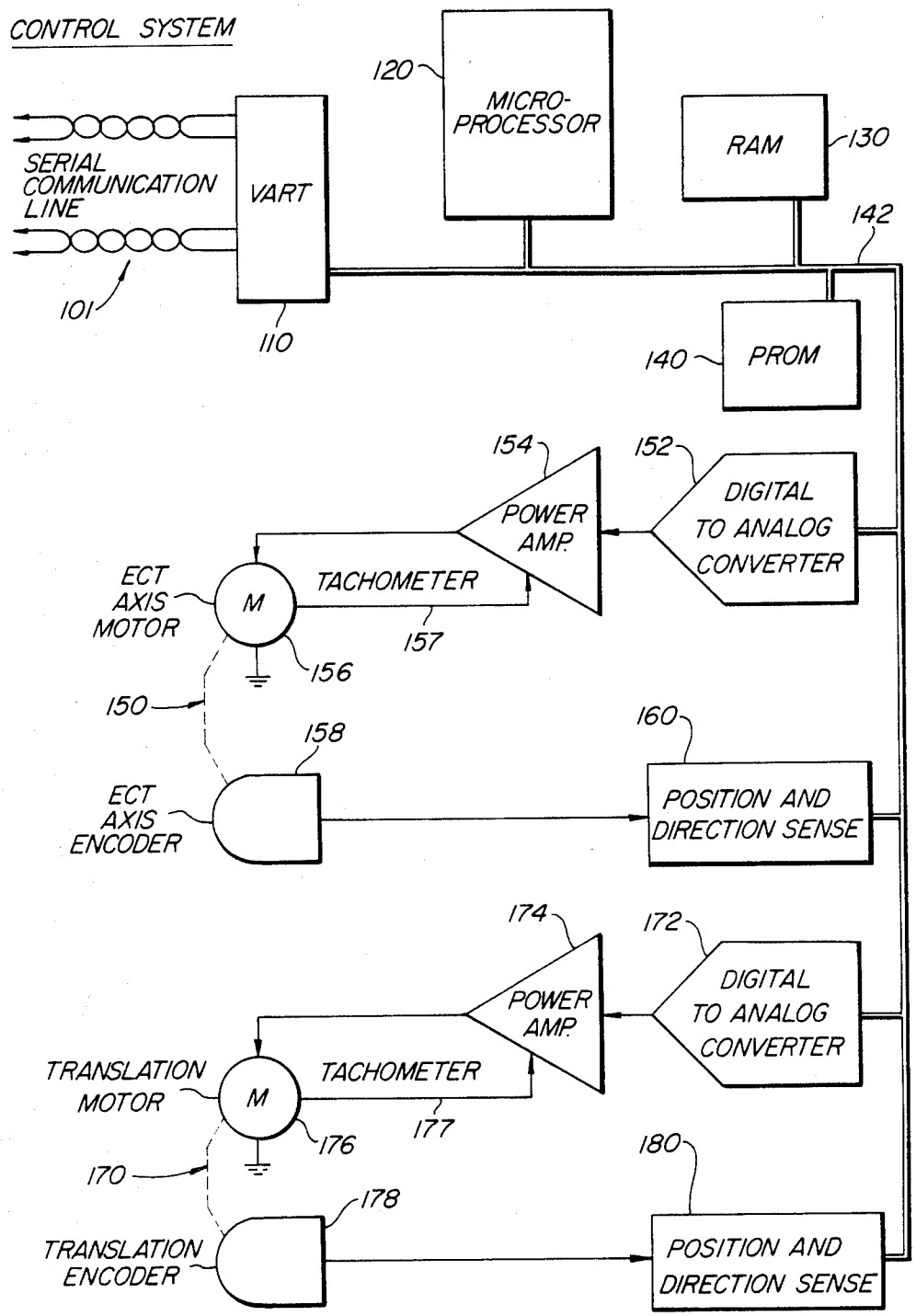
FIG. 5 is a block diagram of a control system in accordance with the present invention.

An example of a control system for implementing a predetermined non-circular ECT imaging path is shown in FIG. 5. The scintillation camera's host computer (not shown) which performs the ECT reconstruction also serves to control this control system via messages transmitted on a serial communication line 101, commonly used to interface teleprinters to computers. A universal asynchronous receiver and transmitter (UART) 110 is provided to encode the serial input data from the serial communication line into a parallel channel 112. A microprocessor 120 receives the encoded messages from the UART and stores received messages in a random access memory (RAM) 130. Software to execute the control system's task by the microprocessor is stored in a programmable read only memory (PROM) 140. Connected to the microprocessor 120 is an ECT rotational sub-system 150 and a linear translation sub-system 170.

The ECT rotational sub-system includes a digital-to-analog converter (DAC) which is arranged to receive a digitized directed number from the microprocessor via data transmission path 112. The sign of the directed number signifies the direction of rotation, whereas the magnitude signifies the rotational velocity. The magnitude of the incremental angular rotation is controlled by the microprocessor which is arranged to count $\frac{1}{8}°$ pulses. The converted analog signal output by the DAC 152 is amplified by a power amplifier 154 and applied to an ECT axis motor 156. The ECT axis motor 156 includes a tachometer winding 157 which is fed back to the power amplifier 154 to maintain the rotational velocity precisely proportional to the DAC 152 output. The ECT axis motor 156 is gear coupled to the carrier member 20, yoke 40 and scintillation detector 50 to effect rotation about the patient. An ECT axis encoder 158 is attached to the ECT rotational axis to serve as an incremental encoder. Encoder 158 provides indication of both rotation rate and direction, supplying a pulse corresponding to every $\frac{1}{8}°$ of rotation. The directed incremental angular rotation information is fed to position and direction sense 160 which is positioned in direct communication relationship with the microprocessor via 112. The position and direction sense electronics communicates rotational direction to the microprocessor. Simultaneously, the microprocessor is counting $\frac{1}{8}°$ pulses and when the proper incremental angular rotation is achieved, the microprocessor issues a command to stop the ECT rotation.

In like fashion, linear translation motion is accomplished under microprocessor control. The linear translation sub-system also includes a digital-to-analog convertor 172 which is arranged to receive a digitized directed number from the microprocessor, wherein the sign of the directed number corresponds to the direction of linear translation of the base and the magnitude corresponds to the velocity of the motion. The extent of the horizontal translation t is controlled by the microprocessor. The output of DAC 172 is amplified by power amplified 174. The amplified analog signal issued by power amplifier 174 is applied to a translation motor 176 which includes a tachometer winding 177 which is fed back to the power amplifier 174 to precisely control the linear velocity proportional to the output of DAC 172. The translation motor 176 is coupled to the base 10 to effect linear translation along the area scan platform between endpoints 16 and 16'. A translation encoder 178 is attached to the area scan path to provide indication of both translation rate and direction. The translation encoder 178 is also an incremental encoder and supplies a pulse corresponding to every incremental horizontal translation (dt) of 0.5 millimeters. A position and direction sense 180 receives the directed encoded information and is arranged for direct communication relationship with the microprocessor via 112. The position and direction sense electronics interrupts the microprocessor as to translation direction. Simultaneously, the microprocessor counts increments (dt) such that when the proper linear distance has been translated, the microprocessor issues a directive to stop the linear translation.

By synchronizing each rotational increment (dθ) by ECT rotational sub-system 150 with each incremental translation dt by linear translation sub-system 170, the desired non-circular ECT rotational orbit is effected.

Implicit in the above description is that the object being scanned remains stationary while the path of the detector is manipulated through a preferential non-circular orbital path. Conversely, the orbit of the detector may be retained circular (i.e., no translation of the base) while the patient is moved to effect the desired minimization of patient-detector distance throughout a tomographic study. For example, the detector 50 may be arranged to orbit the patient by following a circular path of radius r. Whenever, a portion of the patient's thorax lies within that path, the patient is displaced a requisite distance, such as by moving patient support 20 to the right or to the left. The net effect would be identical to the results achieved in the above discussion of FIGS. 3 and 4.

We claim:

1. In a radiographic imaging device of the type having a circularly rotatable scintillation detector adapted for emission computed tomographic imaging of a subject by orbiting about the subject, the improvement comprising:
   (a) means for rotating said scintillation detector predetermined angular increments about the subject along said circular orbit such that a portion of said detector is maintained within a plane defined by said orbit;
   (b) means for displacing the subject relative to the center of radius of said circular orbit during at least a portion of said orbit such that said orbit is maintained within said plane; and
   (c) synchronous control means in communicating relationship with said rotating means and said displacing means for controlling the sequence and duration of said rotation and displacement until a prescribed non-circular planar orbit is circumscribed by said scintillation detector with respect to said subject.

2. In a radiographic imaging device of the type having a circularly rotatable scintillation detector adapted for emission computed tomographic imaging of a subject and a movable base member for supporting said detector and adapted for area scanning studies, the improvement comprising:
   (a) means for rotating said scintillation detector predetermined angular increments along said circular orbit about a longitudinal axis such that a portion of said detector is maintained within a plane defined by said orbit;
   (b) means for moving said base member in directions transverse to said longitudinal axis and in a plane parallel to the plane of said circular orbit predetermined linear increments; and
   (c) synchronous control means in communicating relationship with said rotating means and said translating means for controlling the sequence and duration of said rotation and translation until a prescribed non-circular planar orbit is circumscribed by said portion of said scintillation detector.

3. The apparatus according to claim 2 wherein said rotating means and said translating means are operable in unison.

4. The apparatus according to claim 2 wherein said rotating means and said translating means operate in alternating sequence.

5. The apparatus according to either of claims 3 or 4 wherein said non-circular orbit is traced out intermittently.

6. In an apparatus for supporting and positioning a scintillation detector to a locus of desirable locations relative to a subject to detect radiation emitted by said subject for subsequent reconstruction into a tomogram, said apparatus including a generally C-shaped support member having means for pivotally supporting the scintillation detector at one end portion thereof, a rotatable carrier member slidably engaging said support member for retaining said support member and permitting orbital movement of said support member along a circular path about a section of the subject, the radius of said circular path being determined by the position of said support member relative to said carrier member, a base member for rotatably supporting said carrier member and means for providing linear translation of said base member, the improvement comprising:
   (a) rotational control means coupled to said carrier member for rotating said scintillation detector about said subject along a circular orbit without changing the position of said support member relative to said carrier member;
   (b) translational control means coupled to said base member for translating said scintillation detector predetermined incremental linear distances between a first and a second end point; and
   (c) synchronous control means in communicating relationship with said rotational control means and said translational control means for coordinating said rotation and translation until a prescribed planar non-circular orbit is circumscribed by said scintillation detector.

7. In the apparatus according to claim 6 wherein said rotational control means includes means for controlling the rotational velocity of said carrier member during an incremental rotation and said translational control means includes means for controlling the translational velocity of said base member during an incremental linear translation.

8. In the apparatus according to claim 6 wherein said rotational control means and said translational control means are both under microprocessor control.

9. In the apparatus according to claim 6 wherein said non-circular orbit is traced out in intermittent increments with each increment having at least one of an angular and a linear component and wherein radiation is detected in time between increments.

10. In the apparatus according to claim 6 wherein said non-circular orbit is a step wise alternating linear/circular approximation of an ellipse.

11. A method of non-circular emission computed tomography with a radiographic apparatus having a circularly rotatable scintillation detector comprising the steps of:
   (a) positioning said scintillation detector to transverse in a circle of preselected radius at a desired location and orientation relative to a section of a patient undergoing a tomographic study, the patient having been administered a radionuclide;
   (b) moving said detector in increments along a path about said section, said path having a non-constant center of radius relative to the patient, each increment being the resultant of at least one of:
      (i) rotating said scintillation detector an angular increment along said circle, and
      (ii) displacing said scintillation detector relative to said patient a linear increment; and
   (c) detecting emissions from said patient while said scintillation detector completes a path about said patient at a rate that permits sufficient numbers of gamma rays to be accumulated for reconstructing a tomographic image of the section of the patient being studied.

12. In the method according to claim 11 wherein the relative path of said scintillation detector approximates the boundary of the patient at the tomographic section being studied and wherein the distance between the scintillation detector and the patient is relatively short and generally approximately constant during the path.

* * * * *

UNITED STATES PATENT AND TRADEMARK OFFICE
CERTIFICATE OF CORRECTION

PATENT NO. : 4,503,331
DATED : March 5, 1985
INVENTOR(S) : Richard M. Kovacs, Jr.; Eugene J. Senger;
Robert H. Wake It is certified that error appears in the above—identified patent and that said Letters Patent is hereby corrected as shown below:

col. 6, line 7 "presecribed" should be --prescribed--;

col. 7, line 5 "transverse" should be --traverse--.

Signed and Sealed this

Twenty-second Day of October 1985

[SEAL]

Attest:

Attesting Officer

DONALD J. QUIGG

Commissioner of Patents and
Trademarks—Designate